United States Patent [19]

Ikeda et al.

[11] Patent Number: 4,485,171
[45] Date of Patent: Nov. 27, 1984

[54] MULTI-LAYER MICROORGANISM CULTURE TESTING APPARATUS

[75] Inventors: Tatsuhiko Ikeda, Kawasaki; Takeshi Igarashi, Tama; Atsushi Shimizu, Tokyo, all of Japan

[73] Assignee: Terumo Corporation, Tokyo, Japan

[21] Appl. No.: 416,594

[22] Filed: Sep. 10, 1982

[30] Foreign Application Priority Data

Oct. 13, 1981 [JP] Japan .................. 56-162999

[51] Int. Cl.³ .................. C12M 1/22; C12Q 1/24; C12Q 1/04
[52] U.S. Cl. .................. 435/30; 435/34; 435/298
[58] Field of Search .................. 435/296, 297, 298, 299, 435/4, 30, 34, 18, 23, 24, 231

[56] References Cited

U.S. PATENT DOCUMENTS

| | | | |
|---|---|---|---|
| 2,677,646 | 3/1952 | Lovell et al. | 435/297 |
| 2,761,813 | 9/1956 | Goetz | 435/299 |
| 2,923,669 | 11/1954 | Poitras | 435/34 |
| 3,741,877 | 5/1970 | Shaufus et al. | 435/30 |
| 4,250,256 | 2/1981 | Wielinger et al. | 435/299 |

FOREIGN PATENT DOCUMENTS 2825636 12/1979 Fed. Rep. of Germany ........ 435/34

Primary Examiner—Raymond Jones
Assistant Examiner—Marianne S. Minnick
Attorney, Agent, or Firm—Frishauf, Holtz, Goodman & Woodward

[57] ABSTRACT

A pad assembly for use in a microorganism culture test is provided which comprises, in sterile conditions, a water-absorbing pad which is impregnated with a culture medium for culturing given microorganisms and dried, a filter member bonded to the upper surface of said water absorbing pad and having submicron pores of a size capable of substantially preventing the microorganisms from passing therethrough, and a coating of an antibiotic deactivating agent applied to the upper surface of said filter member or to the common surface between said filter member and said water-absorbing pad, as well as testing apparatus having the pad assembly mounted in a vessel. The invention eliminates the adverse effect of antibiotics in a sample to be tested which will otherwise inhibit the growth of microorganisms in the sample to adversely alter test results.

26 Claims, 7 Drawing Figures

MULTI-LAYER MICROORGANISM CULTURE TESTING APPARATUS

BACKGROUND OF THE INVENTION

Field of the Invention

This invention relates to an apparatus for use in microorganism culture tests of liquid samples containing given microorganisms, and more particularly, to such an apparatus capable of cultivating microorganisms such as bacteria and eumycetes isolatedly from the liquid sample in a simple manner even when the sample contains antibiotics.

Isolation cultures are known in the art. Culture procedures vary depending on the type of sample to be tested. For example, a test on bacteria in blood was carried out by mixing a blood sample with a liquid growth medium. An isolation culture is then carried out in an isolation culture medium such as a blood agar plate and chocolate agar plate. Since it was impossible to directly isolate microorganisms from samples and an extra incubation step was necessary, prior art culturing procedures were rather cumbersome and time consuming. Detection was sometimes impossible when samples contained few microorganisms.

Furthermore, in culture tests of blood samples from septicemia patients, for example, the samples contain antibiotics which have been administered to the patients. These antibiotics significantly inhibit the growth of microorganisms in cultures, adversely affecting the test results. A testing apparatus as disclosed in U.S. Pat. No. 3,741,877 failed to provide accurate test results when samples contained antibiotics. There is a need for a testing apparatus capable of providing accurate test results from antibiotic-containing samples.

SUMMARY OF THE INVENTION

Therefore, an object of the present invention is to provide a multi-layer microorganism culture testing apparatus capable of directly collecting microorganisms from a sample by filtration to allow their culture in isolation without the need for an extra incubation step.

Another object of the present invention is to provide a microorganism culture testing apparatus capable of accurate examination without being affected by the presence of antibiotics in the samples.

According to a first aspect of the present invention, there is provided an improved multi-layer microorganism culture pad assembly for use in tests of liquid samples containing given microorganisms. A water-absorbing pad is impregnated with a culture medium for culturing the microorganisms and then dried. A filter member having submicron pores of a size capable of substantially preventing the passage of these microorganisms therethrough is bondedly laminated on the water-absorbing pad under sterile conditions. An antibiotic deactivating agent is applied under sterile conditions to the surface of the filter member remote from the water-absorbing pad and/or to the common surface between the filter member and the water-absorbing pad to form a coating thereof, completing the assembly. Preferably, the water-absorbing pad has a water-absorbing capacity substantially equal to the amount of liquid sample to be applied to the pad assembly for testing. The culture medium impregnated and dried in the water-absorbing pad is preferably present in an amount capable of forming a liquid culture medium of an acceptable concentration when dissolved in a liquid sample that has penetrated into the pad through said filter member after application to the pad assembly. The pores of the filter member are sized to pass liquid, but to prohibit the microorganisms from passing therethrough, and preferably, have a diameter of 0.22 to 0.75 microns. The filter member is laminated or bonded onto the water-absorbing pad, and preferably, this bonding is achieved with a hydrophilic high-molecular weight adhesive to ensure passage of liquid from the filter member to the water-absorbing member.

The term antibiotic deactivating agent, means an agent capable of deactivating antibiotics likely to be present in a sample, thereby eliminating any inhibition of the growth of microorganisms in the sample by the antibiotics. The antibiotic deactivating agents include agents capable of physically adsorbing antibiotics, agents capable of chemically bonding with antibiotics, and agents capable of decomposing antibiotics.

BRIEF DESCRIPTION OF THE DRAWINGS

The above and other objects, features and advantages of the present invention will be more fully understood from the following description taken in conjunction with the accompanying drawings, in which.

DESCRIPTION OF THE PREFERRED EMBODIMENTS

Figure 1:
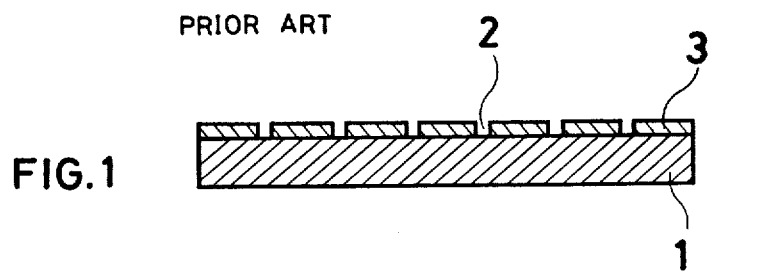
FIG. 1 is a schematic cross-sectional view exaggeratedly showing a prior art multi-layer microorganism culture pad assembly.

The multi-layer microorganism culture pad assembly and the apparatus having the same mounted therein will be further illustrated in connection with a typical example of blood culture by referring to the preferred embodiment shown in the drawings.

Figure 2:
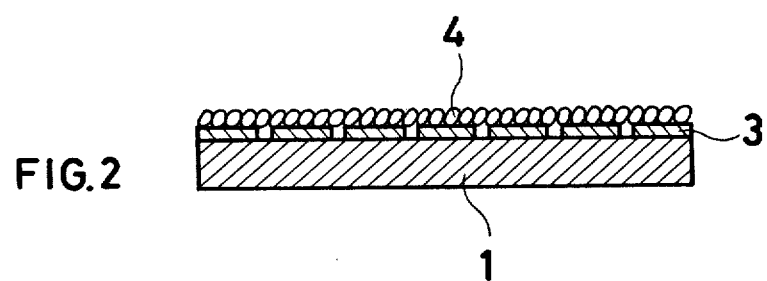
FIGS. 2 and 3 are schematic cross-sectional views of different embodiments of the multi-layer microorganism culture pad assembly of the present invention.
Figure 3:
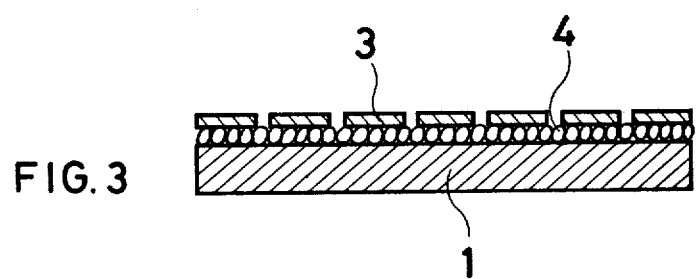

The multi-layer microorganism culture pad assembly of the present invention includes a laminate of a water-absorbing pad 1 which is previously impregnated with a culture medium for culturing given microorganisms and dried, and a filter member 3 laminated or bonded to the water-absorbing pad 1 and having a number of submicron pores 2 of a size capable of substantially preventing the microorganisms from passing therethrough as shown in FIG. 1. The laminate of the water absorbing pad 1 and the filter member 3 is sterilized by any of the conventional methods. This type of laminate is known in the art as disclosed in the above-mentioned U.S. Pat. No. 3,741,877. This laminate type pad assembly was unsuccessful in culturing blood samples taken from septicemia patients since such samples often contained antibiotics. For the purpose of eliminating any influence by antibiotics on microorganism growth, an antibiotic deactivating agent is applied to the upper surface of the filter member 3 as shown in FIG. 2, or to the common surface between the filter member 3 and the water-absorbing pad 1 as shown in FIG. 3 to form a coating 4 thereof, completing the pad assembly of the present invention. In the drawings, the coating 4 is illustrated in an exaggerated and schematic manner.

The materials of which the water-absorbing pad 1 are made are not particularly limited as long as they can absorb aqueous solutions. The preferred materials are cellulosic filter paper, cellulosic unwoven fabric, glass fibers and the like.

The materials of which the filter member 3 are made are not particularly limited as long as they are inert to the samples tested. Typical examples of the filter materials include polycarbonate, polyamide, cellulose esters and the like, commercially available examples being Millipore membrane filter (trade name, Millipore Corporation), Metricell (trade name, German Instrument Company), Saltrius membrane filter (trade name, Karl Zeiss Corporation), and TOYO membrane filter (trade name, Toyo Filter K.K.).

The filter member has a number of submicron pores. If it is important that the filter member functions to isolate any microorganisms in a sample, then a pore diameter of 0.22 microns is most desirable which permits the retention of even *Serratia marcescens*, the smallest microorganism. In practice, however, all microorganisms tested do not pass through the filter member even when the diameter of pores in the filter member is somewhat larger than the size of the smallest microorganism to be examined. Pore diameters of 0.75 microns or less, and especially 0.45 microns or less are preferred because the filter member having pores within this submicron range can retain or isolate essentially all microorganisms while allowing quick permeation of the sample fluid into the underlying pad.

Ordinarily, blood samples taken from septicemia patients contain antibiotics. As described earlier, more accurate results can be obtained from blood cultures by deactivating the coexisting antibiotics. Typically, the antibiotic deactivating agents include:

(1) Antibiotic adsorbing agents (manufactured and sold by Marion Laboratories)
   (a) Cation exchange resins: Polystyrene sulfonate, phenol methylene sulfonate and other types are available. These resins adsorb cationic antibiotics to inhibit their activity.
   (b) Anion exchange resins: Polystyrene amine, phenol formaldehyde polyamine and other types are available. These resins adsorb anionic antibiotics to inhibit their activity.
(2) Chemical bonding agents
   Sodium amylosulfate (SAS, Searle Diagnostics Inc.): This chemically bonds with a variety of antibiotics of aminoglucosides, etc. such as streptomycin, kanamycin, and polymyxin B to deactivate them.
(3) Decomposing agents
   (a) Penicillinase: Penicillinase is a specific enzyme which decomposes penicillin.
   (b) Cephalosporinase: Cephalosporinase is a specific enzyme which decomposes cephalosporin and similar antibiotics.

The culture media with which the water-absorbing pad is impregnated are not particularly limited as long as they are compatible with the samples to be tested. Preferred are those culture media allowing anerobic and aerobic bacteria to grow or propagate under anerobic and aerobic culture conditions, respectively. A typical composition of the culture medium adapted for blood cultures under anerobic and aerobic conditions is shown in Table 1. A test may advantageously be carried out by preparing two multi-layer microorganism culture pad assemblies having such a culture medium impregnated and applying a sample to each pad assembly. One sample may be kept under anerobic culture conditions and the other under aerobic conditions.

TABLE 1

Typical composition of blood culture medium (for filtration of 5-ml sample)

| Ingredient | Amount (mg) |
| --- | --- |
| Trypton (oxoid) | 50 |
| Soy bean pepton (oxoid) | 15 |
| Meat extract (oxoid) | 15 |
| Yeast extract (oxoid) | 25 |
| Liver hydrolyte (oxoid) | 5 |
| Glucose | 12.5 |
| $K_2HPO_4$ | 0.75 |
| NaCl | 20 |
| $NaHCO_3$ | 10 |
| L-Cysteine hydrochloride | 2.25 |
| p-Aminobenzoic acid | 0.25 |
| Hemin | 0.025 |

The water-absorbing pad having an impregnating culture medium dried may be adhesively bonded to the filter member, preferably using a hydrophilic high-molecular weight adhesive such as polyvinyl pyrrolidone.

The thus constructed multi-layer microorganism culture pad assembly of the present invention is not particularly limited in configuration. Most preferably, the pad assembly is circular to match the shape of many implements commonly used in laboratory work, for example, Petri dishes. The size of the pad assembly is also not particularly limited. When 5 ml of a blood sample is applied dropwise onto the pad assembly, the assembly may preferably have a diameter of 60 mm with the pad ranging from 2 mm to 3 mm in thickness.

Figure 5:
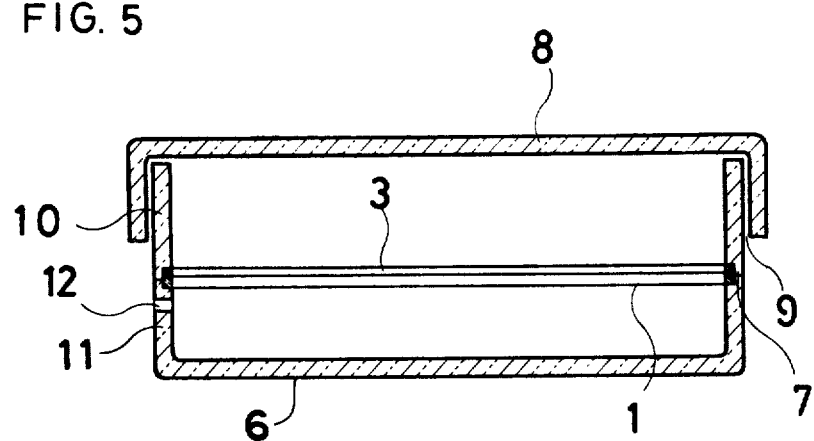
FIG. 5 is a schematic cross-sectional view of a multi-layer microorganism culture testing apparatus of the present invention.
Figure 6:
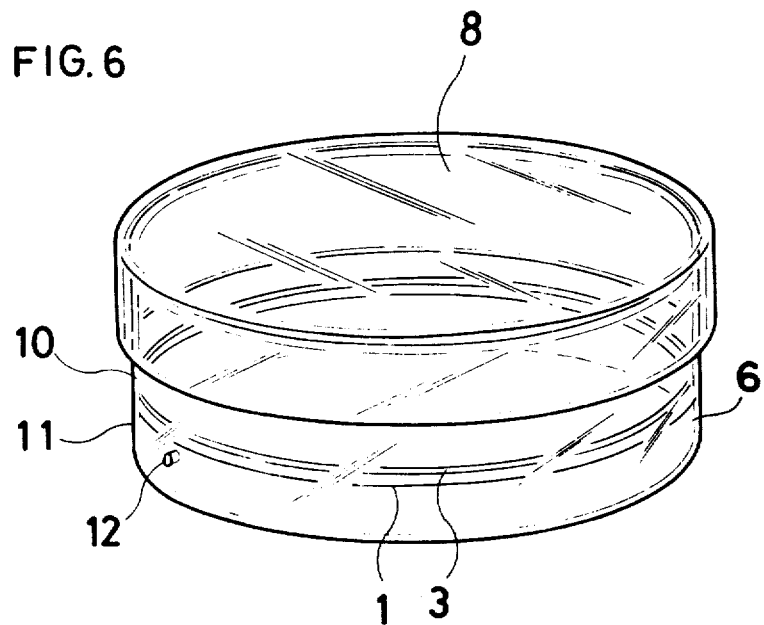
FIG. 6 is a perspective view of the apparatus of FIG. 5.
Figure 7:
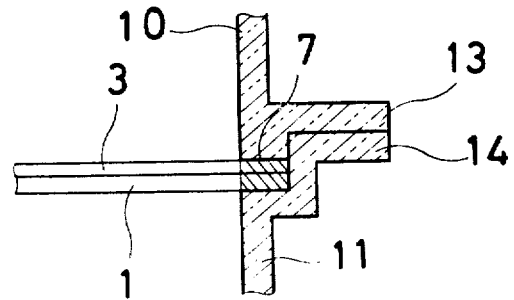
FIG. 7 is a schematic cross-sectional view of the upper and lower sections of the vessel bonded together by an ultrasonic sealing technique.

To facilitate testing, the above-mentioned pad assembly may be mounted in a container of a suitable configuration and size. A typical example of such a container is shown in FIGS. 5, 6 and 7. As seen from the cross-sectional view of FIG. 5, the container consists of a cylindrical vessel 6 having the pad assembly mounted therein and a cap 8 in loose fit on the vessel. It is necessary for effective cultivation that a gap 9 be left between the vessel 6 and the cap 8 to allow airflow. The vessel 6 has a circumferential recess 7 formed at a predetermined height from the bottom so that the pad assembly is firmly held in the recess at the predetermined height. The pad assembly may be mounted in the vessel by placing it in press fit with the recess. Preferably, the vessel 6 is divided into upper and lower sections 10 and 11 which define the recess at their intersection when mated. In this case, the container may be assembled by placing the upper section 10 on the lower section 11 with the pad assembly interposed therebetween, and securing the upper and lower sections to each other. The pad assembly is then rigidly clamped between the upper and lower sections. The distance of the recess 7 from the bottom of the vessel may be determined such that, when a given volume of sample fluid is applied to the pad assembly and excess fluid drips from the pad assembly, the excess fluid that accumulates in the bottom of the vessel does not rise up to the level of the pad assembly positioned in the recess.

Securing or bonding of the upper and lower sections 10 and 11 with the pad assembly clamped therebetween may be carried out by a variety of techniques. For example, the upper and lower sections may be fused to each other by ultrasonic or heat sealing after the pad assembly is interposed between them with no adverse affection to samples to be tested. Alternatively, they may be bonded to each other by applying a solvent capable of dissolving the material of which the vessel is made, or an adhesive comprising such a solvent having the material of which the vessel is made dissolved therein, to the mating edges of the upper and lower sections to thereby partially dissolve the vessel material, eventually forming an integral bond. Of course, the solvent should not inhibit or retard the growth of microorganisms, the preferred examples being methylene chloride and xylene. The material of which the vessel 6 and the cap 8 are made, whether the same or different, may be semi-transparent or preferably transparent for visual observation from the outside. Other requirements are satisfactory hardness, ease of molding and low cost. Typical examples of the vessel and cap forming materials include polystyrene, polyethylene, hard polyvinyl chloride, polycarbonate, methacrylic resins and the like. In case that the upper and lower sections 10 and 11 is bonded by an ultrasonic sealing technique, the upper and lower sections 10 and 11 are provided with mating circumferential flanges 13 and 14, respectively, as shown in FIG. 7.

The lower section 11 of the vessel may be provided with at least one vent 12 for allowing air to escape from the interior of the lower section 11 when sample fluid is applied to the pad assembly (see FIG. 5). However, the vent 12 need not necessarily be formed for the sake of the adequate lower space under the pad assembly.

Figure 4:
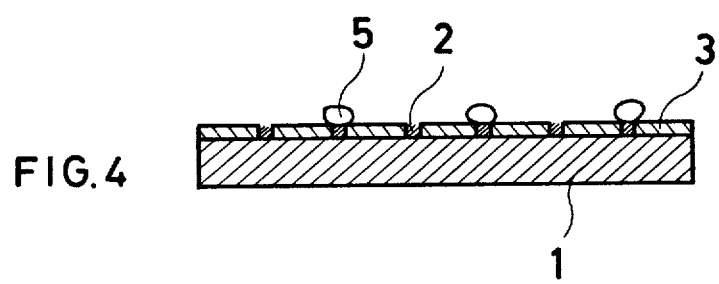
FIG. 4 is a similar cross-sectional view of the culture pad assembly of the present invention showing colonies grown during cultivation.

The multi-layer microorganism culture testing apparatus of the present invention shown in FIGS. 5 and 6 may be used as follows when it is applied, for example, to blood culture. Prior to starting the culture, a liquid sample, i.e., blood is rendered anticoagulative by adding an anticoagulant thereto. A hemolytic agent such as saponin is aseptically added to the sample to fully hemolyze the erythrocytes. The thus treated sample is applied dropwise to the pad assembly in the culture testing apparatus. The microorganisms in the blood sample are isolated or retained by the filter member 3 while the remaining fluid passes through the pores in the filter member 3 to the water-absorbing pad 1 where it dissolves the dried impregnating culture medium to form a liquid culture medium. As described above, for a given volume of sample fluid applied, the water-absorbing pad 1 has an adequate water-absorbing capacity and the culture medium is present in an amount capable of forming a liquid culture medium of a practically acceptable concentration. Thus, according to the present invention, the microorganisms retained above the filter pores will be given an optimum culture medium. Cultivation is carried out under adequate conditions. A culturing test may advantageously be carried out using two sets of testing apparatus each receiving a given volume of sample blood, one being kept under aerobic conditions and the other under anerobic conditions. The thus cultured microorganisms form colonies 5 on the filter member 3 as shown in FIG. 4. The use of the pad assembly of the present invention shown in FIG. 2 or 3 eliminates any adverse influence by antibiotics on the cultivation of microorganisms because the antibiotic deactivating coating adsorbs and removes antibiotics in the blood. When the sample fluid is applied to the pad assembly, excess fluid drips from the pad to the bottom of the container. This prevents the pad from falling down while the purged air may escape through the vent 12, if present.

As is clear from the foregoing, the multi-layer microorganism culture pad assembly and the testing apparatus having the same mounted have the following advantages.

(1) Direct isolation culture is allowable without the need for an extra incubation step as required in prior art cultures, and the culture procedure is considerably simplified.

(2) Since the impregnating culture medium is present in the water-absorbing pad in a dry state, it is highly stable. Conversion of the culture medium from the dry state to the ordinary liquid state may be controlled through adjustment of the water-absorbing capacity of the pad and the amount of the culture medium impregnated. The culture medium becomes restored to the liquid state in which it is ordinarily used after receiving the necessary volume of fluid to ensure consistent culture conditions.

(3) Microorganisms are detectable even at low concentrations.

(4) No extra steps are necessary even when samples contain antibiotics.

What we claim is:

1. A sterilized multi-layer microorganism culture pad assembly for use in determining the presence of microorganisms in a liquid sample comprising:
   a water-absorbing pad containing a dried culture medium for culturing said microorganisms;
   a filter member having a top and bottom surface, said filter member being bonded to said water-absorbing pad at said bottom surface thereof and having pores of a size capable of preventing said microorganisms from passing through said filter member whereby said microorganisms are retained on the surface of said filter member; and
   an antibiotic deactivating agent selected from the group consisting of agents that adsorb antibiotics, agents that chemically bind to antiobiotics and agents that decompose antibiotics, said antibiotic deactivating agent being in contact with at one of said top and bottom surfaces of said filter member.

2. The multi-layer microorganism culture pad assembly of claim 1 wherein said water-absorbing pad has a water-absorbing capacity substantially equal to the amount of liquid in said liquid sample.

3. The multi-layer microorganism culture pad assembly of claim 2 wherein the amount of dried culture medium present in said water-absorbing pad is sufficient to combine with the liquid absorbed by said water-absorbing pad to form a liquid culture medium, said liquid culture medium having a concentration of nutrients sufficient to feed the microorganisms retained on the top surface of said filter member to thereby allow the formation of a colony of said microorganisms.

4. The multi-layer microorganism culture pad assembly of claim 1 wherein said water-absorbing pad containing said dried culture medium is adhesively bonded to the bottom surface of said filter member by a hydrophilic high-molecular weight adhesive.

5. The multi-layer microorganism culture pad assembly of claim 1 wherein the pores of said filter member have a diameter in the range of from 0.22 to 0.75 microns.

6. The multi-layer microorganism culture pad assembly of claim 1 wherein said antibiotic adsorbing agents are selected from the group consisting of anion and cation exchange resins.

7. The multi-layer microorganism culture pad assembly of claim 1 wherein said agents that chemically bind to antibiotics are agents that chemically bind to amino-glucosides.

8. The multi-layer microorganism culture pad assembly of claim 1 wherein said agents that decompose antibiotics are enzymes.

9. An apparatus for use in determining the presence of microorganisms in a liquid sample comprising:
  (a) a sterilized multi-layer microorganism culture pad assembly comprising:
    a water-absorbing pad containing a dried culture medium for culturing said microorganisms;
    a filter member having a top and bottom surface, said filter member being bonded to said water-absorbing pad at said bottom surface thereof and having pores of a size capable of preventing said microorganisms from passing through said filter member whereby said microorganisms are retained on the surface of said filter member; and
    an antibiotic deactivating agent selected from the group consisting of agents that adsorb antibiotics, agents that chemically bind to antibiotics and agents that decompose antibiotics, said antibiotic deactivating agent being in contact with at one of said top and bottom surfaces of said filter member; and
  (b) a container comprising:
    a vessel having a closed bottom end and open top end and side walls connecting said bottom end and said top end for housing said pad assembly, said vessel including means for holding said pad assembly in said vessel at a given height from the bottom end thereof; and
    means for reversibly closing the open end of said vessel.

10. The apparatus of claim 9 wherein said means for reversibly closing the open end of said vessel comprises a cover having side walls extending below and exterior the open end of said vessel when said cover is placed over the top end of said vessel.

11. The apparatus of claim 9 wherein said container is transparent or semi-transparent.

12. The apparatus of 9 wherein said water-absorbing pad has a water-absorbing capacity substantially equal to the amount of liquid in said liquid sample.

13. The apparatus of claim 9 wherein the amount of dried culture medium present in said water-absorbing pad is sufficient to combine with the liquid absorbed by said water absorbing pad to form a liquid culture medium, said liquid culture medium having a concentration of nutrients sufficient to feed the microorganisms retained on the top surface of said filter member to thereby allow the formation of a colony of said microorganisms.

14. The apparatus of claim 9 wherein said water-absorbing pad containing said dried culture medium is adhesively bonded to the bottom surface of said filter member by a hydrophilic high-molecular weight adhesive.

15. The apparatus of claim 9 wherein the pores of said filter member have a diameter in the range of from 0.22 to 0.75 microns.

16. The apparatus of claim 9 wherein said antibiotic adsorbing agents are selected from the group consisting of anion and cation exchange resins.

17. The apparatus of claim 9 wherein said agents that chemically bind to antibiotics are agents that chemically bind to amino-glucosides.

18. The apparatus of claim 9 wherein said antibiotic decomposing agents are enzymes.

19. The apparatus of claim 9 wherein the vessel further comprises at least one air vent in the side wall of said vessel at a position between the bottom end of said vessel and the bottom surface of the pad assembly.

20. The apparatus of claim 9 wherein said means for holding said pad assembly comprises a recess in the side walls of said vessel extending along a plane horizontal to the bottom end of said vessel at said given height thereof, and means on said pad assembly for engaging said recess whereby said pad assembly is held in said recess at said given height from the bottom end of said vessel.

21. The apparatus of claim 20 wherein said pad assembly is bonded to the recess of said vessel.

22. The apparatus of claim 9 wherein said vessel further comprises an upper section comprising said top end of said vessel and a bottom section comprising said bottom end of said vessel, said upper section and bottom section being removably matable with each other; and a recess formed between said upper section and said bottom section when said sections are mated with each other, said recess being adapted to receive said pad assembly whereby said pad assembly is held in said recess at said given height from the bottom end of said vessel.

23. The apparatus of claim 22 wherein said pad assembly is bonded to the recess of said vessel.

24. The apparatus of claim 23 wherein said upper and lower sections further comprise matable circumferential flanges which when mated with each other form said recess.

25. The apparatus of claim 9 wherein the pad assembly has a side surface which conforms to the shape of the interior surface of the side walls of said vessel.

26. The apparatus of claim 25 wherein said vessel and said pad assembly are in the shape of a cylinder.

* * * * *